US006207390B1

(12) United States Patent
Cantor et al.

(10) Patent No.: US 6,207,390 B1
(45) Date of Patent: *Mar. 27, 2001

(54) METHODS FOR THE USE OF REDUCED AFFINITY STREPTAVIDIN

(75) Inventors: Charles R. Cantor, Boston; Takeshi Sano, Waltham, both of MA (US)

(73) Assignee: The Trustees of Boston University, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/941,100

(22) Filed: Oct. 3, 1997

Related U.S. Application Data

(63) Continuation of application No. 08/469,353, filed on Jun. 6, 1995, now abandoned, which is a continuation of application No. 08/420,010, filed on Apr. 11, 1995, now abandoned.

(51) Int. Cl.$^7$ .................................................. G01N 33/53
(52) U.S. Cl. ................................................................ 435/7.1
(58) Field of Search ..................................... 435/7.1, 69.1; 530/350

(56) References Cited

U.S. PATENT DOCUMENTS

| 4,839,293 | * | 6/1989 | Cantor et al. | 435/357 |
| 5,252,466 | * | 10/1993 | Cronan | 435/69.1 |
| 5,328,985 | * | 7/1994 | Sano et al. | 530/350 |

FOREIGN PATENT DOCUMENTS

4135543 * 4/1993 (DE) .

WO8903422 * 4/1989 (WO) .

OTHER PUBLICATIONS

Hendrickson et al. Crystal structure of core streptavidin determined from multiwavelength anomalous diffraction of synchrotron radiation. Proc. Natl. Acad. Sci. USA 86:2190–2194, 1989.*
Weber et al. Structural origins of high–affinity biotin binding to streptavidin. Science 243:85–88, 1989.*
Argarana et al. Nucleic Acids Res. 14(4):1871–1882, 1986.*
Pahler, et al, "Characterization and Crystallization of Core Streptavidin." *J. Biol. Chem*, Oct. 15, 1987, vol. 262 No. 29, pp. 13933–13937.*
"Abstract", Argrana, et al., "Molecular Cloning and Nucleotide Sequence of the Streptavidin Gene", *Nucleic Acids Res.*, Feb. 25, 1986; vol. 14, No. 4, pp. 1871–1882.*
Sano et al., "A streptavidin—metallothionein chimera that allows specific labeling of biological materials with many different heavy metal ions", *Proc. Natl. Acad. Sci., USA*, Mar. 1992, vol. 891, pp. 1534–1538.*
Sano et al., A Streptavidin Mutant Containing a Cysteine Stretch That Facilitates Production of a Variety of Specific Streptavidin Conjugates, *Bio/Technology*, Feb. 1993, vol. 11, pp. 201–206.*
Wilchek, et al., "Avidin—Biotin Technology", *Methods in Enzymology*, 1990, Academic Press, Inc., vol. 184, pp. 5–13.*

(List continued on next page.)

Primary Examiner—Karen Cochrane Carlson
Assistant Examiner—Devesh Srivastava
(74) Attorney, Agent, or Firm—Nixon Peabody LLP

(57) ABSTRACT

The present invention relates to methods for contacting biological targets using a mutated streptavidin protein having a reduced affinity for biotin.

16 Claims, 7 Drawing Sheets (2 of 7 Drawing Sheet(s) Filed in Color)

OTHER PUBLICATIONS

Savage, et al., "Components of Avidin—Biotin Technology", *Avidin–Biotin Chemistry; A Handbook*, Pierce Chemical Company, 1992.*

Sano et al., "Expression of a cloned streptavidin gene in *Escherichia coli*", *Proc. Natl. Acad. Sci., USA*, Jan. 1990, vol. 87, pp. 142–146.*

Sano et al., "Expression Vectors for Streptavidin—Containing Chimeric Proteins", *Biochemical and Biophysical Research Communications*, Apr. 30, 1991, vol. 176, No. 2, pp. 571–577.*

Chilkoti, et al., "Site–directed mutagenesis studies of the high–affinity streptavidin—biotin complex: Contributions of tryptophan residues 79, 108, and 120", *Proc. Natl. Acad. Sci., USA*, Feb. 1995, vol. 92, pp. 1754–1758.*

Wilchek, et al., "Introduction to Avidin–Biotin Technology", *Methods in Enzymology*, Avidin–Biotin Technology, vol. 184, pp. 5–13.*

Zoller, et al., "Oligonucleotide–Directed Mutagenesis of DNA Fragments Cloned into M13 Vectors", *Methods in Enzymology*, (1983) Recombinant DNA Part B, vol. 100, pp. 468–501.*

Phillips, et al., "Isolation of Specific Lymphocyte Receptors by High–Performance Immunoaffinity Chromatography", *Journal of Chromatography*, (1988) vol. 444, pp. 13–20.*

Alon et al., "Cell–adhesive properties of streptavidin are mediated by the exposure of an RGD–like RYD site" *Eur. J. Cell Biol.*, Apr. 24, 1992, vol. 58(2), pp. 271–279.*

Sano, et al., "Intersubunit contacts made by tryptophan 120 with biotin are essential for both string biotin binding and biotin–induced tighter subunit association of streptavidin", *Proc. Natl. Acad. of Science, U.S.A.*, Apr. 1995, vol. 92, pp. 3180–3184.*

Sano, et al., "Recombinant Core Streptavidins" *J. Biol. Chem.* Jul. 26, 1995, vol. 270, No. 47, Issue of Nov. 24, 1995, pp. 28204–28209.*

Matthews, et al., "Introduciton to Proteins: The Primary Level of Protein Structures", Oregon State University *Biochemistry*, Chapter 5, pp. 137–141.*

Gitlin, et al., "Studies on the biotin–binding site of streptavidin", *Biochem. J.* (1988), vol. 256, pp. 279–282.*

Chetverin, et al. "Oligonucleotide Arrays: New Concepts and Possibilities", *Bio/Technology* vol. 12, Nov. 1994, pp. 1093–1099.*

* cited by examiner

SEQUENCE LISTING

```
<160> NUMBER OF SEQ ID NOS: 5

<210> SEQ ID NO 1
<211> LENGTH: 159
<212> TYPE: PRT
<213> ORGANISM: Streptomyces avidinii
<220> FEATURE:
<221> NAME/KEY: UNSURE
<222> LOCATION: (1)
<223> OTHER INFORMATION: The residue in this position can be any amino
      acid.

<400> SEQUENCE: 1

Xaa Pro Ser Lys Asp Ser Lys Ala Gln Val Ser Ala Ala Glu Ala Gly
 1               5                  10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60
```

Ala Thr Asp Gly Ser Gly Thr Ala Leu Gly Trp Thr Val Ala Trp Lys
 65                  70                  75                  80

Asn Asn Tyr Arg Asn Ala His Ser Ala Thr Thr Trp Ser Gly Gln Tyr
                 85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 2
<211> LENGTH: 30
<212> TYPE: DNA
<213> ORGANISM: Streptomyces avidinii

<400> SEQUENCE: 2
accagcgtgg acttgaaggc gttggcctcg                                         30

<210> SEQ ID NO 3
<211> LENGTH: 21
<212> TYPE: DNA
<213> ORGANISM: Streptomyces avidinii

<400> SEQUENCE: 3
aattgctgct gctgctgcta a                                                  21

<210> SEQ ID NO 4
<211> LENGTH: 21
<212> TYPE: DNA
<213> ORGANISM: Streptomyces avidinii

<400> SEQUENCE: 4
gatcttagca gcagcagcag c                                                  21

<210> SEQ ID NO 5
<211> LENGTH: 159
<212> TYPE: PRT
<213> ORGANISM: Streptomyces avidinii

<400> SEQUENCE: 5

Asp Pro Ser Lys Asp Ser Lys Ala Gln Val Ser Ala Ala Glu Ala Gly
 1               5                  10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
 65                  70                  75                  80

Asn Asn Tyr Arg Asn Ala His Ser Ala Thr Thr Trp Ser Gly Gln Tyr
                 85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp

```
                    115                 120                 125
Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155
```

METHODS FOR THE USE OF REDUCED AFFINITY STREPTAVIDIN

This application is a continuation of application Ser. No. 08/469,353, filed Jun. 6, 1995 (now abandoned) which in turn is a continuation of application Ser. No. 08/420,010, filed Apr. 11, 1995 (now abandoned).

RIGHTS IN THE INVENTION

This invention was made with United States Government support under grant number DE-FG02-93ER61656, awarded by the United States Department of Energy, and the United States Government has certain rights in the invention.

BACKGROUND

1. Field of the Invention

This invention relates to recombinant streptavidin proteins having a reduced affinity for biotin and to methods for the binding and release of streptavidin for the detection and isolation of biological agents. The invention also relates to nucleic acids encoding reduced-affinity streptavidin and to recombinant cells which contain and express proteins encoded by these nucleic acids.

2. Description of the Background

Streptavidin, and its functional homolog avidin have been extensively used in biological and medical science due in large part to their ability to specifically bind biotin. Binding has a very high affinity of about $10^{15}$ $M^{-1}$, and is one of the strongest known non-covalent interactions (N. M. Green, Methods Enzymol. 184:5–13, 1990). This extraordinary affinity, coupled with the ability of biotin and its derivatives to be incorporated easily into various biological materials, endows streptavidin-biotin systems with great versatility.

Although avidin and streptavidin have almost the same high affinity for biotin, they are different in many other respects. The two proteins have different molecular weights, electrophoretic mobilities and overall amino acid composition. Avidin is a glycoprotein found in egg whites and the tissues of birds, reptiles and amphibia. Like streptavidin, avidin has almost the same high affinity for biotin and exists as a tetramer with a molecular weight of between about 67,000 to about 68,000 daltons. Avidin also has a high isoelectric point of between about 10 to about 10.5 and contains carbohydrates which cause it to bind non-specifically to biological materials including cell nuclei, nucleic acids and lectins. These non-specific interactions make avidin less suitable than streptavidin for many applications.

Biotin, also known as vitamin H or cis-hexahydro-2-oxo-1H-thieno-(3,4)-imidazole-4-pentanoic acid, is an essential vitamin found in every living cell including bacteria and yeast. In mammals, the tissues having the highest amounts of biotin are the liver, kidney and pancreas. Biotin levels also tend to be raised in tumors and tumor cells. In addition to cells, biotin can be isolated from secretions such as milk which has a fairly high biotin content. Biotin has a molecular weight of about 244 daltons, much lower than its binding partners avidin and streptavidin. Biotin is also an enzyme cofactor of pyruvate carboxylase, trans-carboxylase, acetyl-CoA-carboxylase and betamethylcrotonyl-CoA carboxylase which together carboxylate a wide variety of substrates.

Only the intact bicyclic ring of biotin is required for the strong binding to streptavidin. The carboxyl group of biotin's pentanoic acid side chain has little to contribute to this interaction. Consequently, biotin derivatives, reactive to a variety of functional groups, can be prepared by modifying the pentanoic acid carboxyl group without significantly altering the target's physical characteristics or biological activity. This allows biotin to be conjugated to a number of target molecules.

Streptavidin is produced by the bacteria, *Streptomyces avidini*, and exists as a tetrameric protein having four identical subunits. The full length streptavidin monomer is 159 amino acids in length, some 30 residues longer than avidin. It contains no carbohydrate and has an acidic isoelectric point of about 5.0 which accounts, in part, for the low non-specific binding level. Each subunit of streptavidin is initially synthesized as a precursor of 18,000 daltons which forms a tetramer of about 75,000 daltons. Secretion and post-secretory processing results in mature subunits having an apparent size of 14,000 daltons. Processing occurs at both the amino and carboxyl termini to produce a core protein of about 13,500 daltons, having about 125 to 127 amino acids. This core streptavidin forms tetramers and binds to biotin as efficiently as natural streptavidin. The amino acid sequence of the mature 160 amino acid protein is as follows:

```
1
XPSKDSKAQVSAAEAGITGTWYNQLGSTFIVTAGADGALT         (SEQ ID NO 1)

41
GTYESAVGNAESRYVLTGRYDSAPATDGSGTALGWTVAWK

81
NNYRNAHSATTWSGQYVGGAEARINTQWLLTSGTTEANAW

121
KSTLVGHDTFTKVKPSAASIDAAKKAGVNNGNPLDAVQQ-159
```

The mature streptavidin tetramer binds one molecule of biotin per subunit and the complex, once formed, is unaffected by most extremes of Ph, organic solvents and denaturing conditions. Separation of streptavidin from biotin requires harsh conditions, such as 8 M guanidine, pH 1.5, or autoclaving at 121° C. for 10 minutes.

The advantages of streptavidin-biotin binding systems are numerous. The exceptionally high affinity and stability of the complex ensures complete reaction. Biotin's small size allows it to be conjugated to most molecules with no loss in molecular activity. Multiplicity of biotinylation sites combined with the tetrameric structure of streptavidin allows for amplification of the desired signal. The system is extremely versatile, as demonstrated by the large number of functional targets, binders and probes. The system is amenable to multiple labelling techniques, a wide variety of biotinylated agents and streptavidin-containing probes are commercially available.

Streptavidin-biotin complexes are used in a number of diagnostic and purification technologies. In general, a target molecule to be purified or detected is bound either directly to biotin or to a biotinylated intermediate. The binder may be almost any molecule or macromolecule that will complex with or conjugate to a target molecule. For example, if a particular antigen is the target, its binder would be an antibody. The biotinylated target is bound to streptavidin which may be bound to a probe for ease of detection. This basic technique is utilized in chromatography, cytochemistry, histochemistry, pathological probing, immunoassays, bioaffinity sensors and cross-linking agents, as well as more specific techniques such as targeting, drug delivery, flow cytometry and cytological probing.

The origins of the unusually high binding affinity seen in streptavidin-biotin complexes has not been fully elucidated. X-ray crystallographic studies have shown that streptavidin's carboxyl and amino termini lie on the molecule's surface (P. C. Weber et al., J. Am. Chem. Soc. 114:3197–200, 1992). These termini have been modified by cleavage or conjugation with a minimal effect on biotin binding affinity.

The streptavidin-biotin complex does not involve any covalent bonds, but does contain many hydrogen bonds, hydrophobic interactions and van der Waal interactions. These interactions are largely mediated by the aromatic side chains of tryptophan. Two tryptophan-lysine pairs are conserved between streptavidin and avidin. These pairs are found at positions 79–80 and 120–121 in streptavidin. Additional tryptophan residues in streptavidin are found at positions 92, 108 and 120.

Although participation of tryptophan residues in biotin-binding has been indicated, a quantitative understanding of Trp-120's contribution to biotin-binding has not been reported. Streptavidin's six tryptophan residues per subunit make conventional chemical modifications of any one specific tryptophan residue difficult a situation exacerbated by the tetrameric nature of streptavidin. The Trp-120 of one particular streptavidin subunit makes contact with the biotin bound to an adjacent subunit (A. Pähler et al., J. Biol. Chem 262:13,933–37, 1987). This residue contacts the alkyl moiety of biotin's pentanoyl group in an apparent hydrophobic interaction. Streptavidin's subunit association is made tighter upon biotin-binding (*Advances in Biomagnetic Separation*, T. Sano et al., Eaton Publishing, Natick, Mass., 1994). Because the contact made by Trp-120 to the biotin of an adjacent subunit occurs through the dimer—dimer interface, this residue possibly plays a key role in the biotin-induced tighter association of streptavidin. However, because streptavidin's Trp-120 residue is adjacent to a lysine, both of which are conserved in avidin, lysine may also have a role in binding. Lysine is known to play a critical role in avidin-biotin complex formation. For example, when an avidin lysine at positions 45, 94 or 111 is bound to a dinitrophenyl group, activity is abolished (*Avidin-Biotin Chemistry: A Handbook*, M. D. Savage et al., editors, page 7, 1992).

Trp-120 may play a role in maintaining local structures of streptavidin, particularly around the biotin-binding sites and the dimer—dimer interface. Strong hydrophobicity is observed around Trp-120 and three other tryptophan residues (Trp-79, 92 and 108) that make contact with biotin (P. C. Weber et al., Sci. 243:85–88, 1989; C. E. Argaraña et al., Nuc. Acids Res. 14:1871–82, 1986). In addition, hydrophobic interactions are the major force for the stable association of the two symmetric streptavidin dimers. Changes in local environment caused by the mutation of Trp-120 could prevent the molecule from folding correctly, resulting in diminished biotin-binding ability. In fact, the conversion of some amino acid residues located around the dimer—dimer interface to hydrophilic amino acids causes the formation of insoluble aggregates, probably due to random intermolecular interactions.

Streptavidin's herculean affinity for biotin is unfortunately its major drawback. The streptavidin-biotin binding system is essentially irreversible. The streptavidin-biotin bond is not affected by pH values between 2 to 13, nor by guanidine-HCl concentrations up to 8 M (neutral pH). The half-life for spontaneous dissociation of the streptavidin-biotin bond is about 2.5 years. The extremely strong binding of biotin to streptavidin means that biotinylated proteins can only be recovered from streptavidin supports under denaturing conditions. This sort of system is inappropriate for many procedures such as, one of its principal uses, the purification of delicate proteins. Streptavidin-biotin cannot be used in sequential assays to detect specific types of biomolecules, macromolecular complexes, viruses or cells present in a single sample. The high affinity necessitates the use of harsh chemical reagents, complex procedures, and careful monitoring of the reactions. This also limits both yields and the ability to fully automate such reactions.

A number of methods have been developed in an attempt to create a releasable streptavidin-biotin or avidin-biotin conjugate. These methods include partly monomeric avidin beads, N-hydroxysuccinimide-iminobiotin and biotin or streptavidin cleavage.

Monomeric avidin beads are formed by denaturing tetrameric avidin and coupling the denatured protein to chromatography beads. Thus, the so-called monomeric avidin is really a mixture of monomeric, dimeric and tetrameric proteins that have a binding affinity distributed between the wild type affinity of $10^{15}$ $M^{-1}$ and the reduced affinity of $10^8$ $M^{-1}$. Thus, monomeric avidin beads produce low yields because some of the biotinylated products are irreversibly bound. Furthermore, the density and capacity of monomeric avidin beads is low.

N-hydroxysuccinimide-iminobiotin (NHS-iminobiotin) is a guanido analog of NHS-biotin with a pH sensitive binding annuity for streptavidin. The complete dissociation of NHS-iminobiotin from streptavidin occurs at low pH without the need for strong denaturants. The drawback to the NHS-iminobiotin system is that binding requires a pH of 9.5 or greater, while release requires a pH of less than 4. Thus, the use of NHS-iminobiotin is limited to those few molecules which are stable over a wide pH range.

One method used to dissociate the streptavidin-biotin bond involves proteinase K digestion of streptavidin (M. Wilchek et al., Anal. Biochem. 171:1–32, 1988). However, significant amounts of the streptavidin molecules remain attached even after proteinase K treatment. Proteinase K is useful only when the biotinylated product does not comprise proteins. Furthermore, this system precludes sequential assays or transfers of target.

Another method of release involves biotin cleavage of the binding partners, for example, of a cleavable biotin such as immunopure NHS-SS-biotin which is commercially available (Pierce Chemical Co.; Rockford, Ill.). NHS-SS-biotin consists of a biotin molecule linked through a disulfide bond and an N-hydroxysuccinimide ester group that reacts selectively with primary amines. Using this group, NHS-SS-biotin is linked to a target molecule and the biotin portion removed by thiol cleavage. This complex approach is slow and of limited use since thiols normally disrupt native protein disulfide bonds. Furthermore, cleavage leaves a reactive sulfhydryl group that tends to react with other components of the mixture. Also, thiol-containing nucleic acids will no longer hybridize, severely limiting their usefulness.

SUMMARY OF THE INVENTION

The invention overcomes the problems and disadvantages associated with current strategies and designs and provides a streptavidin protein with reduced affinity for biotin and methods for utilizing reduced affinity streptavidin in detection and isolation.

One embodiment of the invention is directed to reduced-affinity streptavidin protein which comprise an amino acid sequence of streptavidin wherein the protein has a reduced biotin-binding affinity. These proteins contain the sequence of streptavidin which involves the biotin binding site and one or more insertions, deletions or point mutations that reduce the affinity of biotin-binding without severely compromising the ability of streptavidin to bind biotin.

Another embodiment of the invention is directed to recombinant streptavidin proteins which comprise an amino acid sequence of streptavidin wherein the protein has a substantially reduced affinity for biotin. Biotin bind of the recombinant proteins is less than about $10^{12}$ $M^{-1}$. Recombinants proteins may be coupled to solid supports or free in aqueous solutions.

Another embodiment of the invention is directed to proteins which have biotin-binding affinities of between about $10^{12}$ $M^{-1}$ to about $10^7$ $M^{-1}$. These proteins can be fixed to solid supports such as chips and beads for use in detection and isolation procedures.

Another embodiment of the invention is directed to nucleic acids which encode streptavidin proteins having a reduced affinity for biotin. Recombinant nucleic acids may be encoded within plasmids and replicated, chemically synthesized, or transformed into eukaryotic cells.

Another embodiment of the invention is directed to cells which comprise nucleic acids that encode reduced-affinity streptavidin proteins. Cells may be prokaryotic or eukaryotic and may constitutively or inducible express recombinant streptavidin protein.

Another embodiment of the invention is directed to methods for detecting or purifying a target from a heterogenous mixture which contains the target. The target to be purified is biotinylated with biotin or derivative of biotin and contacted to a support to which is attached a reduced-affinity streptavidin protein. The components of the heterogenous mixture can be removed and the target isolated. Alternatively, target may be coupled with reduced-affinity streptavidin and the support coupled with biotin. The target can be purified after contact with the support.

Another embodiment of the invention is directed to methods for targeting a pharmaceutical agent to a cell wherein the agent is coupled to reduced-affinity streptavidin and the cell contains biotin. Such methods can be used to treat or prevent disorders such as infections and neoplasms.

Another embodiment of the invention is directed to kits which contain a streptavidin protein having reduced affinity for biotin and, optionally, additional reagents for the detection or isolation of target substances.

Other embodiments and advantages of the invention are set forth, in part, in the description which follows and, in part, will be obvious from this description and may be learned from the practice of the invention.

DESCRIPTION OF THE DRAWINGS

The file of this patent contains at least one photograph executed in color. Copies of this patent with color photograph(s) will be provided by the Patent and Trademark Office upon request and payment of necessary fee.

DESCRIPTION OF THE INVENTION

Figure 1:
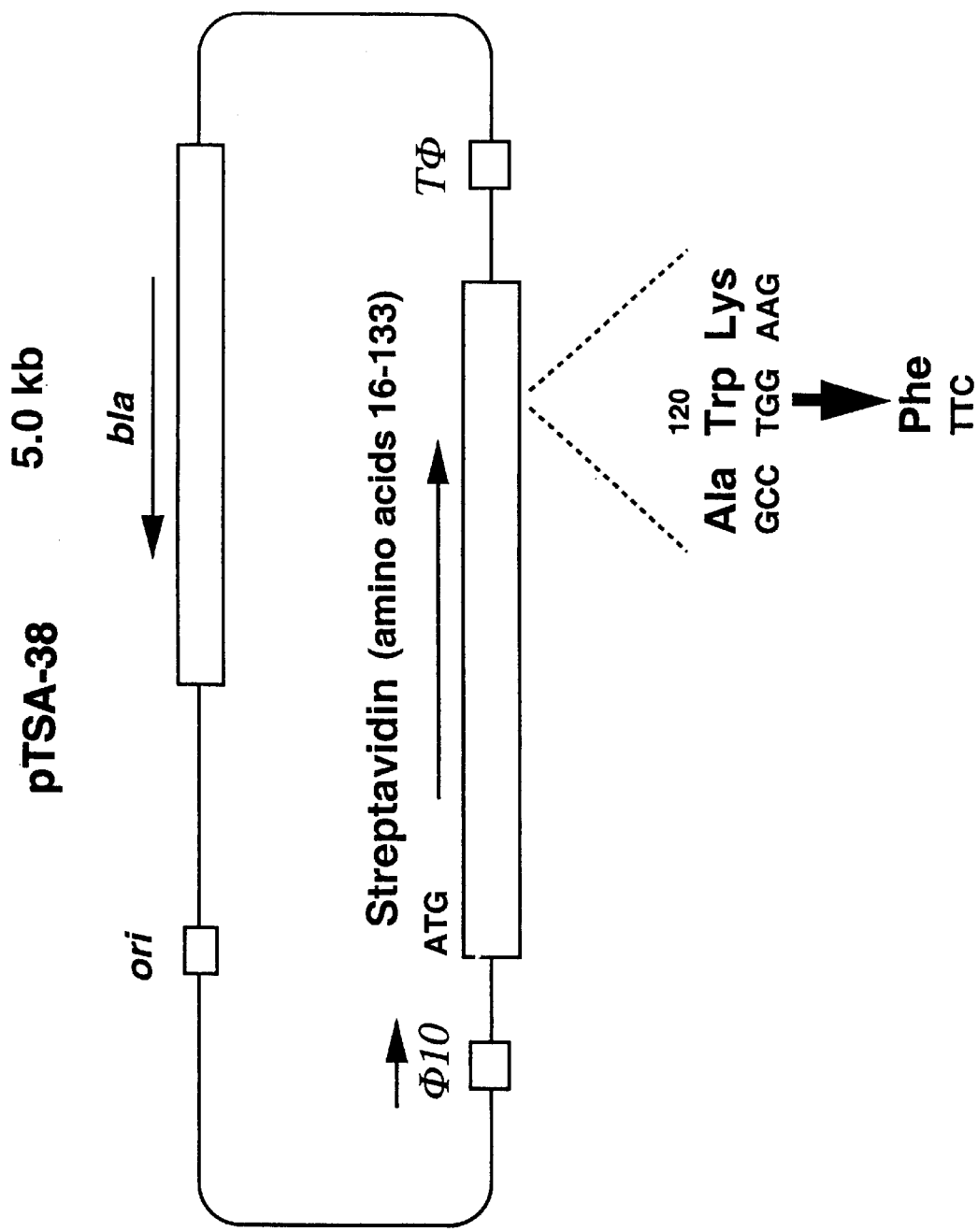
FIG. 1 Schematic of expression vector for a streptavidin mutant with a reduced binding affinity.

As embodied and broadly described herein, the present invention is directed to streptavidin proteins which have a reduced affinity for biotin, to nucleic acid sequences and recombinant cells which contain these sequences, to methods for detecting and isolating small molecules, macromolecules and cells utilizing reduced-affinity streptavidin and to kits which contain reduced-affinity biotin.

The streptavidin-biotin binding system is an established fixture in the biology due, at least in part, to the ability of streptavidin to non-covalently interact with biotin. This association is highly specific and quite strong with a binding constant of greater than $10^{15}$ $M^{-1}$. However, it is precisely this extremely tight binding which limits the usefulness of conventional streptavidin-biotin systems. Although molecules and cells can be isolated from complex mixtures, removal of one or the other of the binding partners is nearly impossible. Dissociation can only be accomplished under very harsh conditions such as 6–8 M guanidinium-HCl pH 1.5. Not surprisingly, such conditions also denature, and thereby inactivate or destroy most target biological substances.

It has been discovered that a streptavidin mutant can be prepared with reduced affinity for biotin while still retaining a very high biotin binding specificity. Complexes formed with these mutants can be disrupted using only gentle treatment. This reduced-affinity streptavidin can be used in all situations which presently take advantage of the properties of wild-type streptavidin (SEQ ID NO:5). Previous difficulties associated with the presence of streptavidin or biotin in complexes are overcome.

One embodiment of the invention is directed to a reduced-affinity streptavidin protein. This protein has a substantially lower binding constant for biotin than wild-type streptavidin (SEQ ID NO:5) and comprises an amino acid sequence of streptavidin containing one or more deletions, insertions, point mutations or combinations of these genetic alterations that alter, but maintain the biotin binding site. The peptide sequence may be a full length streptavidin or an amino acid sequence substantially equivalent to streptavidin. A protein substantially equivalent to streptavidin includes a core streptavidin having the wild-type streptavidin amino acids from about positions 13 to 140, or a reduced-core streptavidin (SEQ ID NO:5) having the wild type streptavidin amino acids from about positions 16 to 133. Other amino acids of streptavidin may be changed without altering the defining characteristic of the reduced-affinity streptavidin.

The streptavidin amino acid sequence of the reduced-affinity protein of the invention may be continuous or fragmented such as, for example, when the protein contains point mutations. Preferably, the protein comprises an amino acid sequence which largely corresponds to the core region of wild-type strep tavidin (SEQ ID NO:5). In the reduced-affinity protein, this region also contains the substitutions or deletion that confer reduced affinity.

One type of reduced-affinity streptavidin protein comprises a core sequence of streptavidin protein (SEQ ID NO:1) wherein one or more of the residues between about position 79 to about position 120 has been substituted or deleted. Within this region are four tryptophans of position 79, 92, 108 and 120, and two tryptophan-lysine pairs (79–80 and 120–121). These sites are extremely hydrophobic and contribute to the biotin binding site. Substitution of, for example, one or more of the tryptophan or lysine residues (or pairs) with an amino acid which is still hydrophobic, but less hydrophobic than tryptophan or lysine, respectively, reduces the affinity of this protein for biotin without destroying the binding site altogether. Amino acids which may be substituted for tryptophan or lysine include methionine, proline, isoleucine, leucine, valine, alanine, glycine, lysine (for tryptophan), phenylalanine, and derivatives and modifications of these amino acids (eg. beta-alanine, N-ethylglycine, 3-hydroxyproline, 4-hydroxyproline, allo-isoleucine, N-methylglycine, N-methylisoleucine, N-methylvaline, norleucine or norvaline). Preferably, the reduced-affinity streptavidin protein comprises a phenylalanine, phenylalanine derivative (e.g. 4-amino-phenylalanine) or a phenylalanine modification (e.g. methylation) at position 79, 92, 108 or 120, and preferably at positions 79 and 120.

The streptavidin protein of the invention has a affinity for biotin of substantially less than wild-type streptavidin (SEQ ID NO:5) or streptavidin core protein. The affinity of these proteins may be less than about $10^{12}$ $M^{-1}$, preferably less than about $10^{10}$ $M^{-1}$, more preferably less than about $10^{9}$ $M^{-1}$, and even more preferably about $10^{8}$ $M^{-1}$. The lower limit of affinity is slightly greater than non-specific binding which can occur at about $10^{6}$ $M^{-1}$ or about $10^{7}$ $M^{-1}$.

Due to the substantial reduction in biotin affinity, as compared to wild-type streptavidin, the streptavidin-biotin bond may be disrupted through the addition of fairly low concentration of biotin or biotin derivatives (biotin analogs) or modifications. The concentration of biotin which can be used to disrupt the reduced-affinity streptavidin-biotin is between about 0.1 mM to about 10 mM or, preferably, between about 0.3 mM to about 2 mM. In addition, elution may be performed in a high pH (e.g. 100 mM triethylamine, pH 11.5; 100 mM phosphate, pH 12.5), in a low pH (e.g. 100 mM glycine pH 4; 100 mM glycine pH 2.5; 100 mM glycine pH 1.8), in high salt (e.g. 5 M LiCl, 10 mM phosphate, pH 7.2; 3.5 M $MgCl_2$, 10 mM phosphate pH 7.2), or in the presence of ionic detergents (e.g. 1% SDS; 1% DOC), dissociating agents (e.g. 2 M urea; 8 M urea; 2 M guanidine HCl), chaotropic agents (e.g. 3 M thiocyanate), organic solvents (e.g. 10% dioxane; 50% ethylene glycol, pH 11.5; 50% ethylene glycol, pH 8), protease (protease K) or water. This type of versatility is a great advantage when utilizing conventional streptavidin-biotin detection or isolation procedures. Proteins are not destroyed and cells remain viable even after biotin has been removed.

Reduced-affinity streptavidin may be bound to a solid support, for example, to facilitate detection and isolation procedures. Typical solid supports include the surfaces of plastic, glass, ceramics, silicone or metal. These components may be found in detection kits, biological sample analysis devices and environmental sampling aids. Particularly useful types of such components include beads, tubes, chips, resins, membranes, monolayers, plates, wells, films, sticks or combinations of the surfaces. Solid supports also include hydrogels which may be made of a variety of polymers such as acrylamide and hydroxyapatite, or biomolecules such as dextran, cellulose or agarose.

Binding of streptavidin to surfaces may be accomplished in several ways. A solid support may be derivatized with a moiety which can form a covalent bond with streptavidin, avidin or biotin. Alternatively many commercially available surfaces may be used to couple streptavidin, avidin or biotin. Example of such surfaces include agarose, cross linked agarose, acrylamide, agarose and acrylamide combinations, polyacrylic, cellulose, nitrocellulose membranes, nylon membranes, silicon and metal. These surfaces may be further modified to contain a carboxyl or other reactive group for crosslinking. Reagents suitable for crosslinking to solid surfaces include cyanogen bromide, carbonyldiimidazole, glutaraldehyde, hydroxysuccinimide and tosyl chloride.

Reduced-affinity streptavidin may also be coupled to a biological agent such as an antibody, an antigen, a hormone, a cytokine or a cell. Cells may be eukaryotic such as mammalian cells, prokaryotic such as bacterial cells, insect cells, parasitic cells, fungal cells or yeast cells. Coupling may be through electrostatic interaction or by covalent modification of one or both coupling partners. Covalent modifications are fairly stable when, for example, the coupled agent is subjected to the a biological environment such as occurs on administration to a host such as a mammal.

Another embodiment of the invention is directed to nucleic acids which encode a reduced-affinity streptavidin protein. Such nucleic acids may further comprise transcription or translational control regions to regulate transcription, translation or secretion of the recombinant protein. Control sequences can also be introduced to provide inducible expression. This is very useful as streptavidin is somewhat harmful to most cells. Recombinant nucleic acids may be introduced into bacterial cells, for example, by transformation, or into mammalian cells, for example, by transfection. Recombinant cells can be used to produce large quantities of recombinant protein as needed or to provide a continuous source of recombinant streptavidin to a biological system.

In conventional streptavidin-biotin systems, there are many methods for detecting or purifying a given target. For example, the target may be directly biotinylated and complexed with the reduced substrate affinity streptavidin. Alternatively a binder that complexes with the target may be the biotinylated component. There may, in fact, be more than one binder involved in a given system. The detectable probe may be bound to the streptavidin and the system may involve more than one detectable probe. Both the target and the support may be biotinylated, and the two are complexed together with the reduced substrate affinity streptavidin. Many permutations are made possible by the variety of targets, binders and probes.

Another embodiment of the invention is directed to a method for detecting or purifying a target from a heterogeneous mixture which contains target. The target is biotinylated using biotin or a biotin derivative or modification appropriate for the target. Targets may be nearly any substance such as biological or inorganic substances. Biological substances include proteins and protein precursors, nucleic acids (DNA, RNA, PNA) and nucleic acid precursors (nucleosides and nucleotides), carbohydrates, lipids such as lipid vesicles, cells, biological samples and pharmaceuticals. Typical proteins which are detectable in conventional streptavidin/biotin systems, and useful herein, include cytokines, hormones, surface receptors, antigens, antibodies, enzymes, growth factors, recombinant proteins, toxins, and fragments and combinations thereof.

Subcellular components may also be purified by linking a ligand, with an affinity to the component, to reduced-affinity streptavidin. Proteins which can be purified include cell adhesion molecules, antibody antigens, receptors ligands and antibodies. Specific affinity adsorbent moieties, such as wheat germ agglutinant, anti-idiotypic antibodies and dye ligands may be coupled to streptavidin to isolate glycosylated proteins such as SP1 transcription factor, dye binding proteins such as pyruvate kinase and liver alcohol dehydrogenase, and other antibodies. Using this method, cellular and subcellular organelles may be rapidly purified using specific antibodies.

The heterogenous mixture is contacted to the reduced-affinity streptavidin which may be fixed to a surface of a support of free in solution. Mixture is removed or the support removed from the mixture and the target purified. Alternatively, target may be coupled to reduced-affinity streptavidin and biotin attached to the support. In either situation, the result is the same. However, using reduced-affinity streptavidin coupled to target, target may isolated free of any biotin.

Using the methods disclosed herein, combination of detection and isolation procedures can also be utilized. For example, targets can be transferred from one support to another using a manual or automated apparatus. Sequential detection or purification techniques can also be used to purify targets to homogeneity. Such techniques were heretofore not possible when the streptavidin biotin bond could not be easily broken. In addition, nearly any conventional detection or isolation methodology can be performed with conventional streptavidin-biotin procedures.

Another embodiment of the invention is directed to a method for the detection of a disorder in a patient such as a human. Reduced-affinity streptavidin is naturally targeted to biotin. Biotinylation of a site within the body of the patient, such as, for example, using monoclonal or polyclonal antibodies coupled with biotin and specific for the site will target the coupled complex to the site. Reduced-affinity streptavidin may be coupled with a pharmaceutical which can be used to treat the disorder. Treatable disorders include neoplasms, genetic diseases and infections (e.g. viral, parasitic, bacterial, fungal).

Another embodiment of the invention is directed to a method for the isolation and culture of infectious agents from a patient. Body fluids, such as blood of a patient may be contacted with a support with antibodies specific for viral surface antigens. If the antibody was crosslinked to the solid support by a reduced-affinity streptavidin, bound infectious agents may be released without harm with a gentle elution technique. The isolated agents may be definitively identified by live culture. Infectious agents which can be isolated by this technique include slow viruses, malaria and infectious yeast.

Another embodiment of the invention is directed to a purification method for nucleic acids and nucleic acid-protein complexes. Nucleic acids can be immobilized to a column through a reduced affinity streptavidin complex. The immobilized nucleic acid may be single or double stranded and it may comprised cloned sequence or random sequence. The column may be used to enrich for nucleic acid-binding proteins. The proteins bound to nucleic acids may be released without the use of nuclease or protease. The product may be studied, without the disruption of the protein nucleic acid bond by native gel electrophoresis (a gel mobility shift assay). This is an especially powerful tool for studying proteins with relatively low affinity for nucleic acids such as transcription factors.

Another embodiment of the invention is directed to methods for using reduced affinity streptavidin to sort cells. Current methods of cell sorting requires a fluorescent activated cell sorter which involves considerable expense and the use of fluorescent dyes which are quite toxic to the cells. Beads and plates coated with antibodies specific for cell surface receptors may can be used to collect cells, but due to the high affinity, the recovery of live cells are generally not feasible. To enhance live release, a reduced affinity antibody may be used but such antibodies also reduce yield. There are many condition where the recovery of live cells is desirable such as in the isolation of hemopoietic stem cells for bone marrow transplants, and the collection of platelet from whole blood for chemotherapy patients. In these situations the reduced affinity streptavidin may be employed to reversibly link antibodies to a surface and the bound cells can be release under non-lethal condition. The released cells may be used directly to treat patients, or the cells can be used as input to further rounds of purification. In addition to antibodies, any moiety which binds tightly to cell surface antigens such as cell adhesion molecules, receptors and, mediators may also be used.

Another embodiment of the invention is directed to the production of macromolecular arrays on solid surfaces using the reduced substrate affinity streptavidin-biotin complex. With reversible complex formation, surface biotinylated probes could be regenerated or changed, as desired, without the use of harsh conditions. This allows the full automation of this, and other, streptavidin application. The reduced substrate affinity streptavidin could also be fused to partner proteins to produce chimeras, in which the streptavidin moiety provides tight, yet reversible binding of the partners to biotin, biotin derivatives, and biotinylated macromolecules. This allows for additional purification and detection techniques, all of which can be fully automated. Thus, reduced substrate affinity streptavidin should be able to serve as a unique biotechnology tool and offer novel applications, in which irreversible biotin-binding by natural streptavidin under the conditions usable with biological materials is undesirable.

Another embodiment of the invention is directed to kits which contain reduced-affinity streptavidin for the detection or isolation of targets, such as substances which may be indicative of a disorder. Disorders which can be detected include infection, neoplastic disorders and genetic defects. Kits may also comprise additional reagents which may be utilized in the detection process.

The following experiments are offered to illustrate embodiments of the invention, and should not be viewed as limiting the scope of the invention.

EXAMPLES

Example 1

Oligonucleotide Directed Mutagenesis of Streptavidin.

To disrupt the inter-subunit hydrophobic contact made by, for example, Trp-120 to biotin without disturbing local environments around this residue, the codon encoding Trp-120 was mutated to a codon encoding phenylalanine. Because of its smaller size, the phenylalanine residue of one subunit should have a considerably reduced hydrophobic interaction, if any, with the alkyl moiety of the pentanoyl group of biotin bound by an adjacent subunit. If no local conformational changes occurred as a result of this mutation, the minimal distance between the phenyl group of this phenylalanine residue and the alkyl chain of biotin should be approximately 5.1 Å. This distance is significantly greater than that between Trp-120 and biotin (4.1 Å) in wild-type streptavidin (SEQ ID NO:5). However, because of the hydrophobicity of phenylalanine, the conversion to Phe-120 should have minimal effects on the local hydrophobic environments around the biotin-binding sites and the dimer—dimer interface.

pTSA-38, which carries the coding sequence for amino acids 16–133 of mature streptavidin (SEQ ID NO:1) was used as the starting material to make reduced affinity streptavidin (FIG. 1). Basically, a phosphorylated oligonucleotide of the sequence 5'-ACCAGCGTGGACTT GAAGGCGTTGGCCTCG-3' (SEQ ID NO 2) was used to mutate the codon TGG encoding for Trp on residue 120 to TTC. The new codon TTC, codes for Phe at position 120. Briefly, the reaction was initiated by hybridizing 10 pmoles of the phosphorylated oligonucleotide to the single stranded streptavidin DNA in a 10 µl reaction with 20 mM Tris-HCl, pH 7.5, 10 mM MgCl$_2$, 50 mM NaCl and 1 mM dithiothreitol (DTT). Elongation and mutation was initiated by the addition of 10 µl of 20 mM Tris-HCl, pH 7.5, 10 mM MgCl$_2$, 10 mM DTT, 2 mM dATP, 2 mM dTTP, 2 mM dCTP, 2 mM dGTP, 10 mM ATP, 5 units bacteriophage T4 DNA ligase and 2.5 units of Klenow. Products created after 15 hour of incubation at 16° C. were used to transform competent *E. coli* cells. To ensure that the clones contained the desired mutations, the sequence was confirmed using a dideoxy chain termination procedure.

Example 2
Production of Phe-120 Streptavidin in *E. coli*.

The mutated streptavidin of Example 1 were used to produce large quantities Phe-120 streptavidin protein. Because the expression of streptavidin in bacteria has a lethal effect to a cell, an inducible system was used. The DNA fragment comprising the sequence encoding the streptavidin mutant was excised from its vector with the restriction endonucleases Nde1 and BamH1, and cloned into the same sites in the T7 expression vector pET-3a. Resultant plasmids were transfected in BL21(DE3)(pLysE) bacteria.

To produce the Phe-120 streptavidin, BL21(DE3)(pLysE) cells carrying the expression plasmid were grown at 37° C. in LB supplemented with 0.4% glucose, 150 µg/ml ampicillin and 25 µg/ml chloramphenicol until cultures reach a density of 0.6 at A$_{600}$. Expression of the Phe-120 streptavidin was induced by the addition of a gratuitous inducer, IPTG, to a final concentration of 0.4 mM. Phe-120 streptavidin was expressed for five hours at 37° C. before the cells were harvested.

Example 3
Purification of Expressed Phe-120 Streptavidin.

Phe-120 streptavidin protein produced by induced *E. coli* was purified. Cells expressing the mutant streptavidin were harvested by centrifugation at 1600×g for 10 minutes. Protein was purified from the insoluble fraction of cell extracts. Briefly, cells were pelleted, washed with an isotonic solution of 100 mM NaCl, 1 mM EDTA and 10 mM Tris, pH 8.0, and resuspended in a detergent solution of 2 mM EDTA, 30 mM Tris-HCl, pH 8.0, 0.1% Triton X-100. Lysis occurred under these conditions because the presence of T7 lysozyme in the cells.

Nucleic acid in the extract was digested for 15 minutes at room temperature by the addition of MgSO$_4$, DNase I and RNase A, to final concentrations of 12 mM, 10 µg/ml and 10 µg/ml, respectively. The insoluble fraction of the extract containing Phe-120 streptavidin was isolated by centrifugation of the nuclease treated extract at 39,000×g for 15 minutes. Pellets were washed with 2 mM EDTA, 30 mM Tris-HCl, pH 8.0, and 0.1% Triton X-100, and solubilized in 6 M guanidine hydrochloride, pH 1.5.

Impurities were removed by dialysis against 6 M guanidine hydrochloride pH 1.5. Mutant streptavidin was renatured slowly by dialysis against 0.2 M ammonium acetate, pH 6. After renaturation, insoluble impurities were removed by centrifugation at 39,000×g. Supernatant containing the mutant streptavidin protein was removed and collected. Final purifications were performed by 2-iminobiotin affinity chromatography.

Example 4
General Characteristics of the Phe-120 Streptavidin.

Figure 2A:
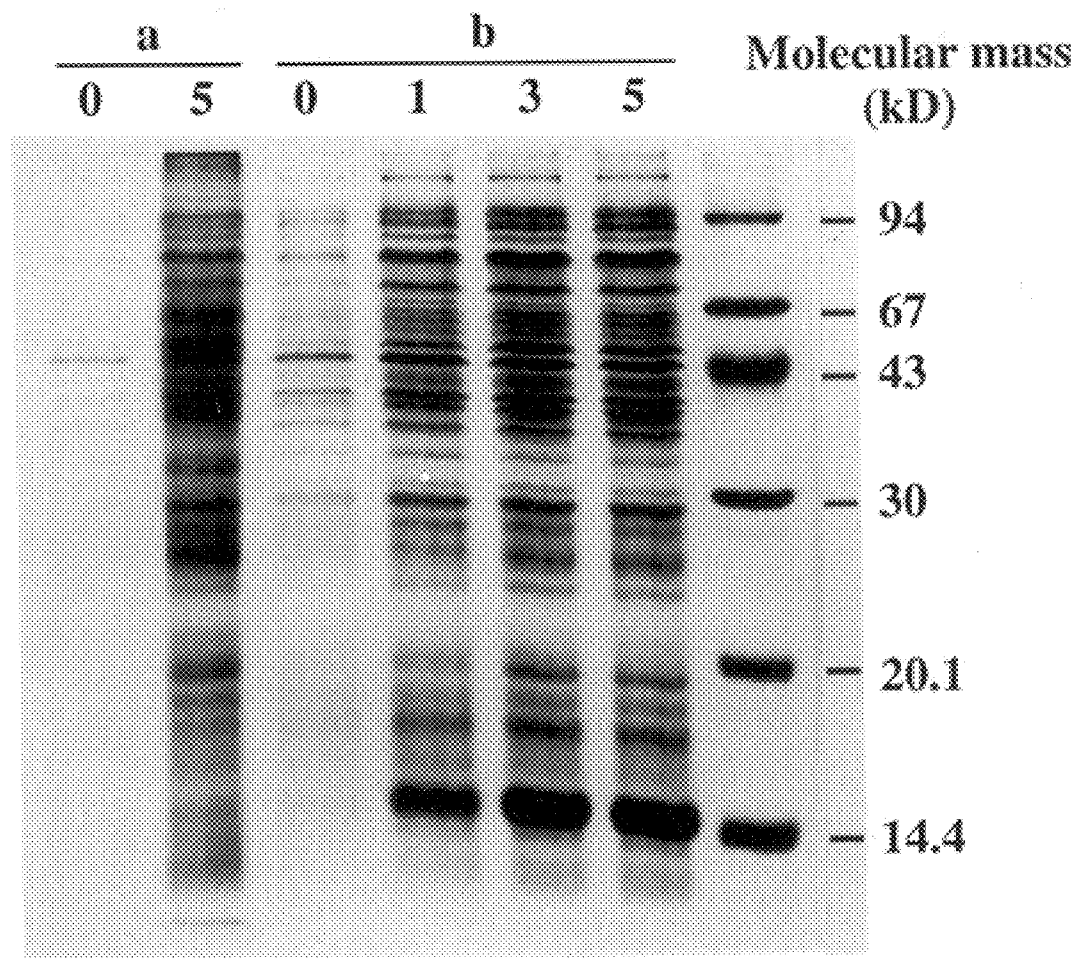
FIG. 2A Presents the SDS gel electrophoresis pattern observed from expression vector pTSA-38.

Polyacrylamide gel electrophoresis analysis (PAGE-SDS) of the subunit molecular mass of Phe-120 streptavidin was performed on protein expressed in *E. coli* from pTSA-38. Total cell protein of BL21(DE3)(pLysE), with or without pTSA-38, was analyzed using a 15.% polyacrylamide gel. As shown in FIG. 2A, lanes "a"=BL21(DE3)(pLysE) and lanes "b"=BL21 (DE3)(pLysE)(pTSA-38), streptavidin protein could be easily visualized upon staining. The number above each lane is the time in hours after induction. Each lane contained total cell protein from the following volume of culture: At 0 hour for "a" and, at 0 hour and 1 hour for "b", 50 µl; at 3 hours and 5 hours for "b", 33 µl; and at 5 hours for "a", 25 µl. The right lane contains molecular mass standard proteins.

Figure 2B:
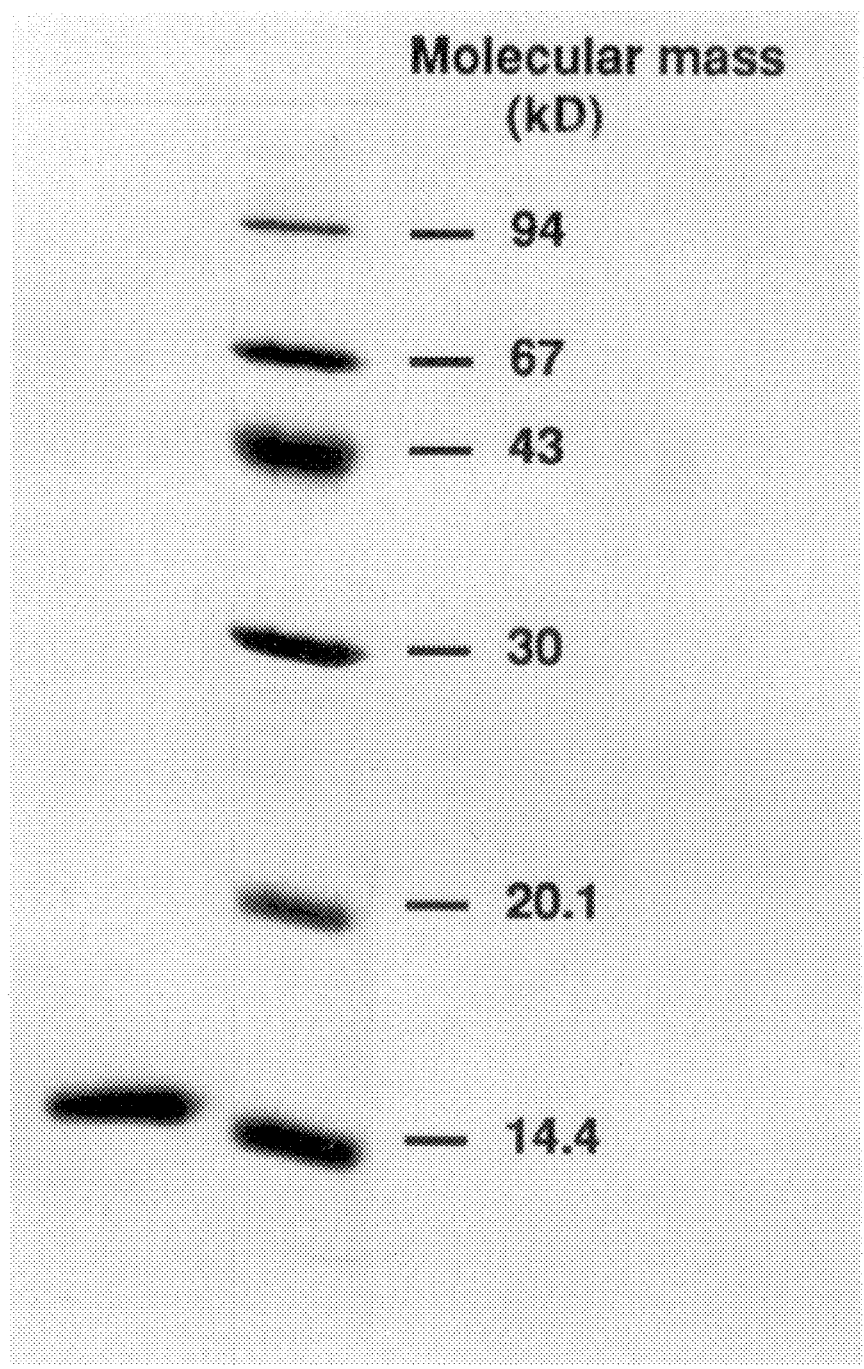
FIG. 2B Presents the SDS gel electrophoresis pattern observed from purified pTSA-38 expression product.

Purified Phe-120 streptavidin was also analyzed by SDS-PAGE. Briefly, approximately 3 µg of purified Phe-120 streptavidin was applied to a 15% polyacrylamide gel (FIG. 2B). The right lane contains molecular mass standard proteins. The molecular weight of Stv-38 was estimated to be approximately 13,000 daltons, which is consistent with the molecular mass obtained from the deduced amino acid sequence (12,600 daltons).

Figure 3A:
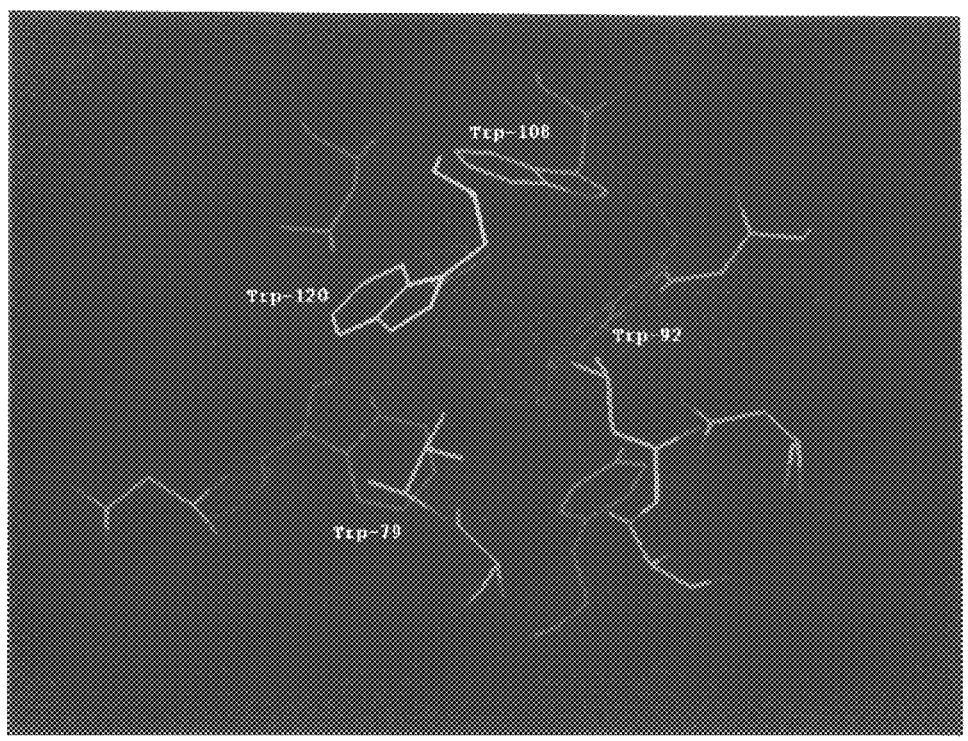
FIG. 3A Presents the local structures around the biotin-binding site of natural streptavidin.
Figure 3B:
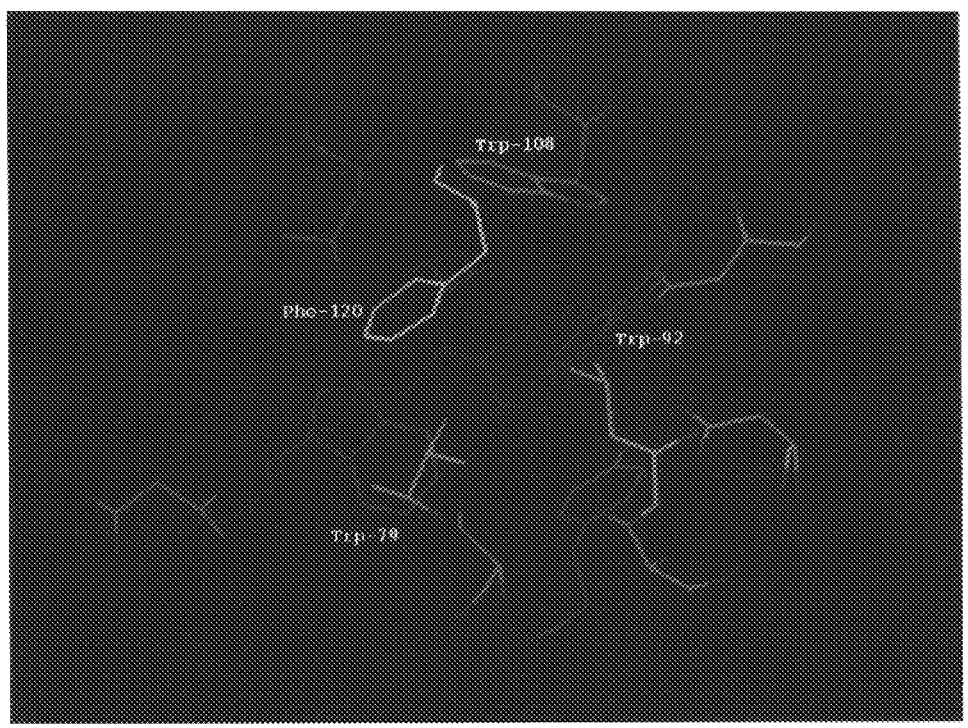
FIG. 3B Presents the local structures around the biotin-binding site of reduced-affinity streptavidin protein.

Local structures around the biotin-binding site of streptavidin are shown in FIG. 3A, the natural or wild-type streptavidin (SEQ ID NO:5), and FIG. 3B, the reduced-affinity streptavidin of Stv-38 in which Trp-120 is converted to Phe. Bound biotin is colored red. These structures are drawn based on the known three-dimensional structure of natural streptavidin. The positions of the four Trp residues (Trp-79, -92, -108 and -120) are indicated. Note that Trp-79, -92 and -108 are of one subunit with biotin, while Trp-120 (yellow) or Phe-120 (yellow) is provided by an adjacent subunit through the dimer—dimer interface. Carbon, nitrogen, and oxygen atoms are colored green, blue and red, respectively.

Example 5
Biotin Binding of Phe-120 Streptavidin.

On gel filtration chromatography using a Superdex 75 HR 10/30 column the molecular mass of purified Phe-120 was estimated to be 49,0000 daltons, consistent with proper tetramer formation. Biotin bound Phe-120 was isolated also by Superdex 75 HR 10/30 column. When the biotin bound Phe-120 was analyzed, biotin was found at an amount of greater than 0.97 molecules of biotin per streptavidin subunit. This degree of binding is consistent with full biotin-binding ability. These results indicate that Phe-120 streptavidin forms a tetramer as does wild type streptavidin (SEQ ID NO:5) and that the conversion of Trp-120 to Phe-120 has no significant effect on the basic properties of the mutant streptavidin. These data also indicate that the mutation had minimal effects on local environments around the biotin-binding sites and the dimer—dimer interface, thus allowing the correct folding of the molecule.

Example 6

Determining the Biotin-Binding Affinity of the Phe-120 Streptavidin.

The biotin-binding affinities of wild type and Phe-120 streptavidin were determined by an equilibrium dialysis method using a micro dialyzer (Hoeffer Scientific). One hundred microliters each of D-[carbonyl-$^{14}$C] biotin (2 nM–4 µM; 53 mCi/mmol; Amersham) and 100 µl of streptavidin (5.3 µg/ml, 0.42 µM subunits) were prepared separately in TBS (150 mM NaCl, 20 mM Tris-HCl, pH 7.4, 0.02% NaN$_3$) solutions. Equilibrium dialysis analysis was begun by the placement of the two solutions into two opposing chambers of a micro dialyzer. Chambers were incubated at 30° C. with rotation for 48 hours and the concentration of labeled biotin in each chamber was measured by scintillation counting. Results were plotted on a Scatchard plot. The apparent biotin-binding affinity of the Phe-120 streptavidin was determined to be from about 1–3×10$^8$ M$^{-1}$ demonstrating the reduced substrate affinity of this streptavidin mutant.

Comparison with the biotin-binding affinity of natural core streptavidin (4×10$^{14}$ M$^{-1}$ at pH 7.0 at 25° C.) indicated that a substantial reduction in the biotin-binding affinity was caused by the mutation of Trp-120 to Phe. This indicated that the hydrophobic contact made by Trp-120 to biotin contributed significantly to the extremely tight biotin-binding by streptavidin. Disruption of the hydrophobic contact made by Trp-120 to biotin may not be solely responsible for the drastic reduction in biotin-binding affinity. The mutation of Trp-120 to Phe-120 may have generated additional structural changes in or around the biotin-binding site which also lowered the biotin-binding affinity.

Example 7

Determination of Biotin-Binding Stability.

To determine if the mutation affected the biotin-binding stability of streptavidin, stability was determined by monitoring the release of radioactive biotin in the presence of free biotin at neutral pH. Purified Phe-120 streptavidin was saturated with D-[carbonyl-$^{14}$C] biotin in 150 mM NaCl, 20 mM Tris-HCl, pH 7.4, 0.2 mM NaN$_3$. Stv-38 was mixed with D-[carbonyl-$^{14}$C]biotin at a molar ratio of biotin to biotin-binding site of 1. This Stv-38 solution (1.71 µg, 136 nmol subunits in 133 µl of TBS) was mixed with an equal volume (133 µl) of TBS containing various concentrations of free biotin. The mixture was allowed to stand at 21° C. for 20 minutes, transferred to a Ultrafee MC filter (molecular mass cut off, 10 kD), and centrifuged at 1,600×g for 10 minutes.

Stability of the biotin-bond was measured by counting the amounts of released radioactive biotin in the filtrate. The amount of radioactivity in the filtrates was determined by liquid scintillation counting, and plotted as a function of the final concentration of free biotin added (FIG. 4; closed square), and the amount of natural core streptavidin analyzed in the same manner as the control (FIG. 4; open circle).

Figure 4:
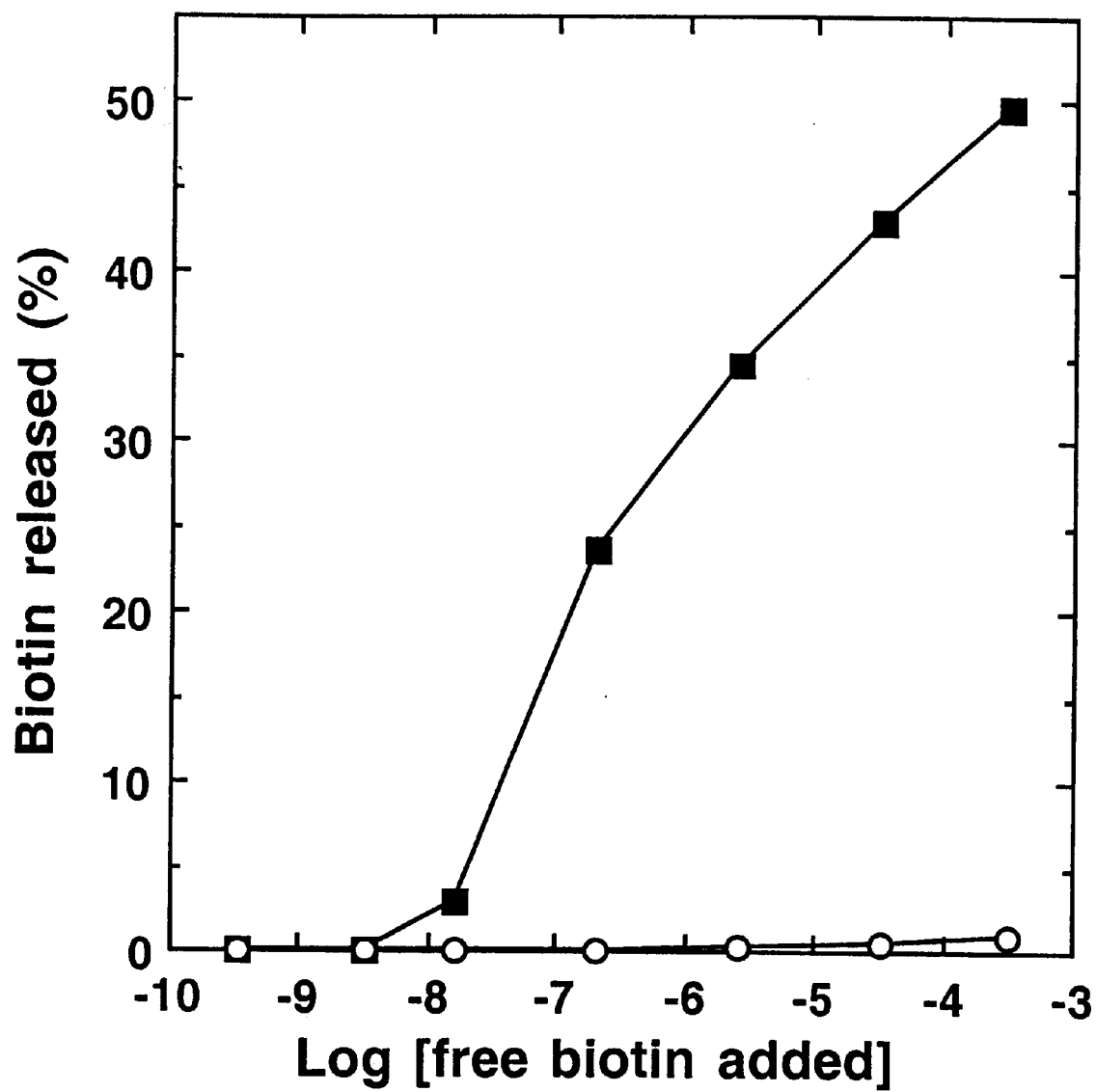
FIG. 4 Graph showing release of biotin from reduced-affinity streptavidin protein in relation to increased amounts of added free biotin.

As shown in FIG. 4, the amount of released $^{14}$C-labeled biotin increased as the concentration of free biotin was raised above 33 nM. Addition of 330 µM free biotin released approximately 50% of the bound $^{14}$C-labeled biotin from Phe-120 streptavidin. In contrast, almost no release of bound biotin was observed with natural core streptavidin by the addition of free biotin up to 330 µM.

These results demonstrated that Phe-120 streptavidin retains bound biotin stably even under relatively harsh conditions. However, the addition of free biotin resulted in the dissociation of previously bound biotin from the mutant due, presumably, to exchange of bound biotin with free biotin.

In the three-dimensional structure of streptavidin, Trp-120 spatially covers the pentanoyl group of bound biotin. This apparently contributes to the very low dissociation rate constant for streptavidin-biotin complexes (2.8×10$^{-6}$ sec$^{-1}$ at pH 7 at 25° C.)$^3$. It is quite likely that the mutation of Trp-120 to Phe-120 led to the greater rate constant for the dissociation of bound biotin with minimal effects on the association rate constant, thereby enhancing exchange reactions with free biotin.

Example 8

Effect of Biotin Binding on Subunit Association.

Figure 5:
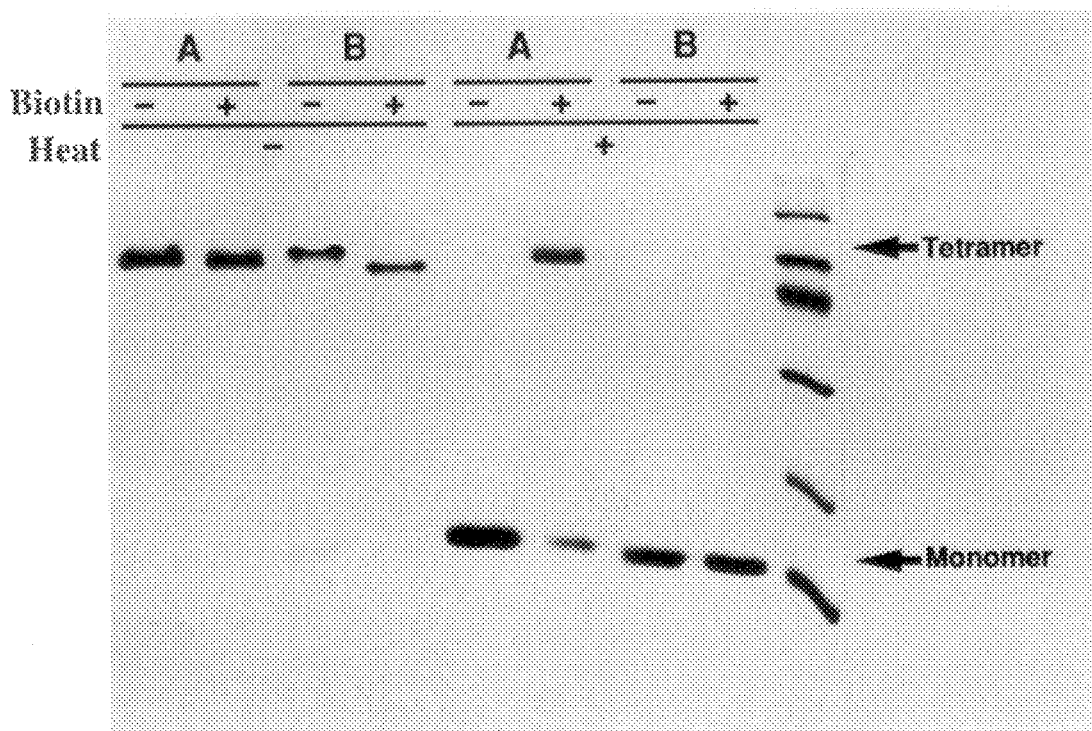
FIG. 5 Effects of biotin binding on subunit association.

Because the hydrophobic contact made by Trp-120 to biotin occurs through the dimer—dimer interface, this inter-subunit communication may contribute to the biotin-induced tighter subunit association of streptavidin, which is observed in core streptavidin. To test this possibility, the subunit association of Phe-120 streptavidin with and without biotin was investigated by SDS-PAGE (FIG. 5).

Natural core streptavidin (5.0 µg; 0.37 nmol subunits) (FIG. 5, lanes marked A) or Stv-38 (4.0 µg; 0.32 nmol subunits) (FIG. 5, lanes marked B), in 4 µl of TBS, was mixed with an equal volume of TBS without or with 1.7 nmol biotin (molar ratio of biotin to subunit, 4.6 for natural core streptavidin and 5.3 for Stv-38), and the mixtures incubated at 21° C. for 5 minutes. To each of these mixtures (8 µl), 2 µl of 3.0% SDS, 100 mM Tris-HCl, pH 6.8, and 40% glycerol were added to a final SDS concentration of 0.6%. The resulting samples were either incubated at 21° C. for 5 minutes or heated in boiling water for 3 minutes, and subjected to SDS-PAGE.

Upon heat treatment in the presence of SDS, wild type core streptavidin and Phe-120 streptavidin, both without biotin, dissociate completely into monomers. However, the dissociation of natural core streptavidin was partly repressed by biotin-binding, and two distinct protein bands corresponding to the tetramer and monomer were observed. In contrast, no tetramer band was observed with Phe-120 streptavidin even in the presence of biotin under the same conditions, indicating that its subunit association was not tightened significantly upon biotin-binding. This demonstrated that the inter-subunit contact made by Trp-120 to biotin was the primary force that induced the tighter subunit association of natural streptavidin upon biotin-binding.

Even without heat treatment, a part of Phe-120 streptavidin dissociated into monomers in the presence of SDS, while no dissociation was observed with wild type core streptavidin. Biotin-binding had only a slight effect on the dissociation of Phe-120 streptavidin without heat treatment. This indicated that Trp-120 also contributes to the subunit association of tetramers in the absence of biotin.

Because hydrophobic interactions around the dimer—dimer interface are the major force for stable association of two symmetric dimers, the reduction in hydrophobicity around the dimer—dimer interface, caused by the mutation of Trp-120 to Phe, would also reduce the overall stability of the dimer—dimer association.

Example 9
Crosslinking Streptavidin to a Solid Support.

Reduced substrate affinity streptavidin was dialyzed extensively against binding buffer (0.5 M sodium phosphate, pH 7.5) to remove inhibitors before attaching to solid supports. Cyanogen bromide activated beads (Pharmacia Biotech; Piscataway, N.J.) were washed with 100 volumes of binding buffer to remove preservatives and used immediately for coupling. Mutant streptavidin was crosslinked to the beads by adding the activated beads to the mutant streptavidin and mixing gently overnight at room temperature. Uncrosslinked mutant streptavidin was removed by washing the beads with binding buffer followed by a solution of 1 M NaCl and 0.05 M sodium phosphate, pH 7.5. Unreacted groups were blocked by incubating the beads in 100 mM ethanolamine, pH 7.5, for 4 hours with gentle mixing. After ethanolamine was removed by washes with phosphate buffered saline (PBS; 0.144 g/L $KH_2PO_4$, 9 g/L NaCl, 0.795 g/L $Na_2HPO_4$-$7H_2O$), the reduced substrate affinity streptavidin coupled beads were ready for use.

Example 10
Separation of Biotinylated from Non-Biotinylated Proteins.

A chromatography column is used for separation of a biotinylated protein from a mixture of proteins. Reduced substrate affinity streptavidin coupled beads are poured into the column and washed with 5 column volumes of phosphate buffered saline (PBS). The protein mixture is added to the column and the biotinylated proteins are adsorbed to the column for 30 minutes. The non-biotinylated proteins are washed away with PBS. Biotinylated protein is removed from the column with a wash solution of PBS containing biotin at a concentration of 500 $\mu$M.

Example 11
Cell Sorting: Isolation of Human T and B Cells.

Bone marrow transplants are sometimes helpful in the treatment of cancers, particularly leukemia. However, there are very few stem cells in the blood and a cell sorting method will be useful in their isolation. Reduced affinity streptavidin may be used to isolate a specific cell population from blood. The isolation of B cells and T cells from blood is used as an example. Lymphocytes are prepared from whole blood by gradient separation using a Ficoll-Paque® gradient (Pharmacia Biotech; Piscataway, N.J.) and resuspended in a final cell concentration of $10^8$ per ml. One ml of purified lymphocytes and 2 mls of glass beads coated with reduced substrate affinity streptavidin is used for T and B cell isolation.

Two mls of reduced substrate affinity streptavidin coated glass beads are placed into a 3 ml column. Beads are washed with 10 mls of PBS and air bubbles in the column bed removed by centrifuging columns at 1000×g for 10 minutes. Ten mg of purified biotinylated goat anti-human IgG (heavy and light chain) (Pierce Chemical Co.; Rockford, Ill.) in PBS are applied to the column. Antibody is absorbed to the beads at room temperature for one hour in a rotator. Unbound antibodies are removed by washing the column with 30 mls of PBS.

Cell sorting is performed by applying the lymphocytes to the column at 500 $\mu$l per minute and collect the flow through fraction which contains the T cells. Additional T cells are removed by washing the column with 15 mls of PBS at 500 $\mu$l per minute. Optimal yield and separation of B cells and T cells are dependent on a constant flow rate. The optimal flow rate for a 2 ml column should be less than about 5 mls per minute and about 500 $\mu$l per minute. Eluate from loading and washing fraction contains the T cells. B cells are eluted from the column with 15 mls of 2 mM Biotin in PBS.

Example 12
Multiple Detection Techniques: Multiple Westerns.

An oncogene expression profile of a tumor can be determined by successive probing of a western blot using a variety of antibodies conjugated to $^{125}$I-labeled streptavidin. Briefly, 500 $\mu$Ci of $^{125}$I-labeled N-succinimidyl 3-(4-hydroxyphenyl propionate) (ICN Radiochemicals; Irvine, Calif.) in dimethylformamide is air dried to the bottom of a tube. Radiolabeling is initiated by the addition of 10 $\mu$g of reduced substrate annuity streptavidin in 10 $\mu$l of 0.1 M sodium borate to the tube. Mutant streptavidin is labeled on ice for 15 minutes and the reaction terminated with 100 $\mu$l of 0.5 M ethanolamine, 10% glycerol, 0.1% xylene cylanol and 0.1 M sodium borate, pH 8.5. Labeled streptavidin is separated from the labeling reagent on a gel filtration column.

Biotinylated anti-myc antibody and biotinylated anti-ras antibody are labeled individually by contacting the antibody with $^{125}$I-labeled streptavidin. A western blot having multiple lanes of total proteins from tumors is probed with the $^{125}$I-labeled anti-myc antibody. Briefly, 10 mls PBS, with 3% dried milk and 1 $\mu$g/ml anti-myc antibody is contacted with the blot for one hour with agitation. The non-specific binding is washed away with PBS. Myc expression is detected by an autoradiograph of the blot. The $^{125}$I labeled streptavidin is removed by washing the blot with PBS and 2 mM biotin. Biotin is removed by washing the blot with PBS. Ras expression can be detected by repeating the procedure with an anti-ras antibody. A profile of oncogene expression in multiple tumors is revealed in successive autoradiographs.

In addition to western blots, this multiple probing technique may also be used for dot and s lot blots, nucleic acid blots (Northern, Southern), Histology section probed with antibodies, karyotype hybridization (Chromosome spread), expression library screening with antibodies, cDNA library screening with nucleic acid probes and far-western blots with labeled protein.

Example 13
Deletion of Residues 113–120.

To increase solubility and to reduce biotin binding affinity, a hydrophobic stretch is removed from streptavidin. The starting material for creation of a streptavidin deletion mutant is a single stranded DNA preparation of a vector with an insert encoding amino acid 16 to 133 of streptavidin (pTSA-18F, T. Sano et al. Bio/Technology 11: 201–6, 1993). The mutation is created with a phosphorylated oligonucleotide, comprising a sequence complementary to the single stranded DNA both 5' and 3' to the desired deletion region. This oligonucleotide is used to remove codons encoding amino acids 113 to 120. Briefly, the reaction is initiated by hybridizing 10 pmoles of the phosphorylated mutagenic oligonucleotide and 10 pmoles of the nonphosphorylated universal sequencing primer to the single stranded M13 streptavidin DNA in a 10 $\mu$l reaction comprising 20 mM Tris-HCl, pH 7.5, 10 mM $MgCl_2$, 50 mM NaCl and 1 mM dithiothreitol. Elongation and mutation is initiated by the addition of 10 $\mu$l comprising 20 mM Tris, pH 7.5, 10 mM $MgCl_2$, 10 mM DTT, 2 mM dATP, 2 mM dTTP, 2 mM dCTP, 2 mM dGTP, 10 mM ATP, 5 units bacteriophage T4 DNA ligase and 2.5 units Klenow fragment of DNA polymerase I. The product is used to transform competent E. coli cells after a 15 hour 16° C. incubation. This deletion mutant is increased in stability in aqueous solutions.

Example 14
Mutation of Codon 127 to Aspartic Acid.

An acidic residue is added to streptavidin to stabilize the dimeric and heterotetrameric forms of streptavidin. A single stranded DNA preparation of the resulting plasmid of Example 13, encoding core streptavidin with codons 113 to 120 deleted, is used as the starting material for this mutation. A single stranded DNA preparation is performed using *E. coli* as the host bacteria. An oligonucleotide, complementary to the single stranded DNA and encoding for aspartic acid at codon 127 of the streptavidin gene is synthesized with an oligonucleotide synthesizer and phosphorylated. Except for this mutagenic oligonucleotide, the procedure used for this mutagenesis is identical to oligonucleotide-directed deletion of residues 113 to 120. This procedure resulted in the production of a gene encoding core streptavidin with a deletion of codon 113 to 120, and with aspartic acid at residue 127. The sequence of the resulting plasmid is confirmed by DNA sequencing using a dideoxy termination method. This gene is cloned into a bacterial expression vector and the mutated streptavidin expressed and purified. This streptavidin mutant dimerizes in aqueous solutions, has a reduced biotin binding affinity of less than $10^8$ $M^{-1}$, and can form heterodimers with the mutant streptavidin of Example 15.

Example 15
Mutation of Codon 127 to Lysine.

A basic residue is added to streptavidin to stabilize the dimeric and heterotetrameric forms of streptavidin. A single stranded DNA preparation of the resulting plasmid of Example 13, encoding core streptavidin with codons 113 to 120 deleted, is used as the starting material. An oligonucleotide, complementary to the single stranded phage DNA and encoding for lysine at codon 127 of the streptavidin gene is synthesized with an oligonucleotide synthesizer and phosphorylated. Except for this mutagenic oligonucleotide, the procedure used for this mutagenesis is identical to oligonucleotide-directed deletion of residues 113 to 120. This procedure resulted in the production of a gene encoding core streptavidin with a deletion of codon 113 to 120, and with Aspartic acid at residue 127. The sequence of the resulting plasmid is confirmed by DNA sequencing using a dideoxy termination method. This gene is cloned into a bacterial expression vector and the mutated streptavidin is expressed and purified. This streptavidin mutant dimerizes in solution and forms a heterotetramer with the mutated streptavidin of Example 14. The biotin binding affinity of this mutant is less than $10^8$ $M^{-1}$.

Example 16
Addition of 5 Cysteines to Core Streptavidin.

Cysteine residues are added to the carboxyl terminus of streptavidin to allow conjugation to other molecules through sulfhydryl reactions. A plasmid DNA, encoding residues 16 to 112 and 121 to 133 of streptavidin with Lys at position 127 from example 15 is used as the starting material. Plasmid is digested with EcoRI and BamHI. Two 21 mer oligonucleotides, 5'-AAT TGC TGC TGC TGC TGC TAA-3'(SEQ ID NO 3), 5'GAT CTT AGC AGC AGC AGC AGC-3'(SEQ ID NO 4) are annealed, and the resulting double-stranded DNA inserted and ligated into the Eco RI and Bam HI sites of the predigested plasmid. The sequence of the resulting plasmid is confirmed by DNA sequencing using a dideoxy termination method. This gene is cloned into a bacterial expression vector and the mutated streptavidin expressed and purified. This streptavidin mutant has all the properties of the streptavidin mutant of Example 15. It dimerizes in solution, forms heterodimers with the streptavidin mutant of Example 14, and has a reduced biotin-binding affinity of less than about $10^8$ $M^{-1}$. In addition, this streptavidin mutant may be conjugated to other proteins and macromolecules, and also solid supports through the sulfhydryl group on the cysteines.

Other embodiments and uses of the invention will be apparent to those skilled in the art from consideration of the specification and practice of the invention disclosed herein. The specification and examples should be considered exemplary only with the true scope and spirit of the invention indicated by the following claims.

We claim:

1. A method for contacting a target, comprising a) providing a target to be biotinylated and biotinylation means; b) biotinylating said target with said biotinylation means under conditions such that a heterogeneous mixture is created, said heterogeneous mixture comprising target and biotinylated target; and c) contacting said heterogeneous mixture with a solid support, said solid support comprising a reduced-affinity streptavidin protein, wherein said reduced-affinity streptavidin protein has an amino acid sequence that is different from the amino acid sequence of wild-type streptavidin (SEQ ID NO:5), and wherein the difference between said reduced-affinity streptavidin protein and said wild-type streptavidin (SEQ ID NO:5) comprises deletions of residues 113–120 from the 16–133 fragment of said wild-type streptavidin.

2. The method of claim 1 wherein said target is selected from the group consisting of proteins and protein precursors, nucleic acids and nucleic acid precursors, carbohydrates, cells, lipid vesicles, and pharmaceuticals.

3. The method of claim 1 wherein said target is a protein and the protein is selected from the group consisting of cytokines, hormones, surface receptors, antigens, antibodies, enzymes, growth factors, recombinant proteins, toxins, and fragments thereof.

4. A method for contacting a target, comprising a) providing a target to be biotinylated and biotinylation means; b) biotinylating said target with said biotinylation means under conditions such that a heterogeneous mixture is created, said heterogeneous mixture comprising target and biotinylated target; and c) contacting said heterogeneous mixture with a solid support, said solid support comprising a reduced-affinity streptavidin protein, wherein the difference between said reduced-affinity streptavidin protein and wild-type streptavidin (SEQ ID NO:5) comprises a phenylalanine substituted for a tryptophan at positions 79, 92, 108, or 120 of said wild-type streptavidin (SEQ ID NO:5) such that said reduced-affinity streptavidin protein displays reduced-affinity for biotin.

5. The method of claim 4 wherein said target is selected from the group consisting of proteins and protein precursors, nucleic acids and nucleic acid precursors, carbohydrates, cells, lipid vesicles, an pharmaceuticals.

6. The method of claim 4 wherein said target is a protein and the protein is selected from the group consisting of cytokines, hormones, surface receptors, antigens, antibodies, enzymes, growth factors, recombinant proteins, toxins, and fragments thereof.

7. The method of claim 4 wherein said solid support is selected from the group consisting of surfaces of plastic, glass, ceramics, silicone, metal, cellulose, and gels.

8. The method of claim 4 wherein said solid support is selected from the group consisting of beads, tubes, chips, resins, plates, wells, films, and sticks.

9. A method for contacting a target, comprising a) providing a target to be biotinylated and biotinylation means; b) biotinylating said target with said biotinylation means under conditions such that a heterogeneous mixture is created, said heterogeneous mixture comprising target and biotinylated target; and c) contacting said heterogeneous mixture with a solid support, said solid support comprising a reduced-affinity streptavidin protein, wherein said reduced-affinity streptavidin protein has an amino acid sequence that is different from the amino acid sequence of SEQ ID NO:1, and wherein the difference between said reduced-affinity streptavidin protein and said SEQ ID NO:1, comprises deletions of residues 113–120 from the 16–133 fragment of said amino acid sequence of SEQ ID NO: 1.

10. The method of claim 9 wherein said target is selected from the group consisting of proteins and protein precursors, nucleic acids and nucleic acid precursors, carbohydrates, cells, lipid vesicles, and pharmaceuticals.

11. The method of claim 9 wherein said target is a protein and the protein is selected from the group consisting of cytokines, hormones, surface receptors, antigens, antibodies, enzymes, growth factors, recombinant proteins, toxins, and fragments thereof.

12. A method for contacting a target, comprising a) providing a target to be biotinylated and biotinylation means; b) biotinylating said target with said biotinylation means under conditions such that a heterogeneous mixture is created, said heterogeneous mixture comprising target and biotinylated target; and c) contacting said heterogeneous mixture with a solid support, said solid support comprising a reduced-affinity streptavidin protein, wherein the difference between said reduced-affinity streptavidin protein and the amino acid sequence of SEQ ID NO:1 comprises a phenylalanine substituted for a tryptophan at positions 79, 92, 108, or 120 of said amino acid sequence of SEQ ID NO: 1 such that said reduced-affinity streptavidin protein displays reduced-affinity for biotin.

13. The method of claim 12 wherein said target is selected from the group consisting of proteins and protein precursors, nucleic acids and nucleic acid precursors, carbohydrates, cells, lipid vesicles, and pharmaceuticals.

14. The method of claim 12 wherein said target is a protein and the protein is selected from the group consisting of cytokines, hormones, surface receptors, antigens, antibodies, enzymes, growth factors, recombinant proteins, toxins, and fragments thereof.

15. The method of claim 12 wherein said solid support is selected from the group consisting of surfaces of plastic, glass, ceramics, silicone, metal, cellulose, and gels.

16. The method of claim 12 wherein said solid support is selected from the group consisting of beads, tubes, chips, resins, plates, wells, films, and sticks.

* * * * *